United States Patent
Levin et al.

(10) Patent No.: US 6,297,406 B1
(45) Date of Patent: Oct. 2, 2001

(54) PRODUCTION OF PHENOL

(75) Inventors: Doron Levin, Bala Cynwyd; Jose G. Santiesteban; James C. Vartuli, both of West Chester, all of PA (US)

(73) Assignee: Mobil Oil Corporation, New York, NY (US)

( * ) Notice: Subject to any disclaimer, the term of this patent is extended or adjusted under 35 U.S.C. 154(b) by 0 days.

(21) Appl. No.: 09/366,249

(22) Filed: Aug. 3, 1999

(51) Int. Cl.⁷ .................................................. C07C 37/08
(52) U.S. Cl. ........................... 568/798; 568/385; 568/768; 568/754; 568/741

(58) Field of Search .................................... 568/385, 798, 568/768, 756, 741

(56) References Cited

U.S. PATENT DOCUMENTS

| | | | |
|---|---|---|---|
| 4,490,565 | 12/1984 | Chang et al. | 568/798 |
| 4,490,566 | 12/1984 | Chang et al. | 568/798 |
| 4,898,995 | 2/1990 | Knifton et al. | 568/798 |
| 5,908,800 | 6/1999 | Bonneau et al. | 501/103 |

*Primary Examiner*—Sreeni Padmanabhan

(57) ABSTRACT

A process for producing phenol and acetone from cumene hydroperoxide is described in which the cumene hydroperoxide is contacted with a solid-acid catalyst comprising a mixed oxide of cerium and a Group IVB metal.

10 Claims, No Drawings

PRODUCTION OF PHENOL

BACKGROUND OF THE INVENTION

1. Field of the Invention

This invention relates to the production of phenol and more particularly to a process for producing phenol and acetone from cumene hydroperoxide.

2. Description of the Prior Art

Phenol is an important organic chemical with a wide variety of industrial uses. It is used, for example, in the production of phenolic resins, bisphenol-A and caprolactam. A number of processes are currently in use for the production of phenol but the single process providing the largest proportion of the total production capacity is the cumene process which now accounts for over three quarters of the total U.S. production. The basic reaction involved in this process is the cleavage of cumene hydroperoxide into phenol and acetone:

$$C_6H_5C(CH_3)_2OOH = C_6H_5OH + (CH_3)_2CO$$

On the industrial scale, the cumene hydroperoxide is usually treated with dilute sulphuric acid (5 to 25 percent concentration) at a temperature of about 50° C. to 70° C. After the cleavage is complete, the reaction mixture is separated and the oil layer distilled to obtain the phenol and acetone together with cumene, alpha-methylstyrene, acetophenone and tars. The cumene may be recycled for conversion to the hydroperoxide and subsequent cleavage. The phenol produced in this way is suitable for use in resins although further purification is required for a pharmaceutical grade product.

Although the process described above is capable of producing both phenol and acetone in good yields, it would be desirable to find a process which would reduce the need for the product separation and purification steps which are inherent in a homogeneous process and would avoid the need for environmentally hazardous liquid acids.

The heterogeneous cleavage of cumene hydroperoxide (CHP) over various solid acid catalysts has already been reported. For example, U.S. Pat. No. 4,490,565 discloses the use of zeolite beta in the cleavage of cumene hydroperoxide, whereas U.S. Pat. No. 4,490,566 discloses the use of a Constraint Index 1–12 zeolite, such as ZSM-5, in the same process.

U.S. Pat. No. 4,898,995 discloses a process for the coproduction of phenol and acetone by reacting cumene hydroperoxide over a heterogeneous catalyst consisting essentially of a heteropoly acid, such as 12-tungstophosphoric acid, on an inert support, such as silica, alumina, titania and zirconia. Such heteropoly acid catalysts are inherently unstable at temperatures in excess of 350° C.

U.S. Pat. No. 5,908,800 discloses a process for producing a mixed zirconium and cerium oxide useful as a catalyst for reducing nitrogen oxides in automotive exhaust by contacting a liquid mixture of cerium and zirconium compounds with carbonate and bicarbonate under neutral or alkaline conditions to form a precipitate comprising cerium carbonate and zirconium oxyhydroxide, and then calcining the precipitate.

According to the invention, it has now been found that a solid acid catalyst comprising mixed oxides of cerium and a Group IVB metal can exhibit activity and selectivity for cumene hydroperoxide cleavage.

SUMMARY OF THE INVENTION

The present invention resides in a process for producing phenol and acetone from cumene hydroperoxide, wherein the process comprises the step of contacting cumene hydroperoxide with a solid-acid catalyst comprising a mixed oxide of cerium and a Group IVB metal.

Preferably, Group IVB metal is zirconium.

Preferably, said solid acid catalyst also contains a further metal selected from Group IB, VIIB and VII metals, and preferably selected from iron, manganese and copper.

Preferably, the solid acid catalyst is produced by calcining a catalyst precursor comprising a source of a Group IVB metal oxide with a source of cerium oxide at a temperature of at least 400° C.

Preferably, said temperature is at least 500° C. and more preferably is 600–700° C.

Preferably, said catalyst precursor is precipitated from a liquid mixture containing ions of cerium and said Group IVB metal at a pH less than 9, and more preferably, 3 to 8.

Preferably, said contacting step is conducted at a temperature of 20 to 150° C. and a pressure of atmospheric to 1000 psig and more preferably at a temperature of 40 to 120° C. and a pressure of atmospheric to 400 psig.

The process of the invention can achieve significant conversion of cumene hydroperoxide to phenol and acetone with low coproduction of impurities such as mesityl oxide and diacetone alcohol.

DESCRIPTION OF SPECIFIC EMBODIMENTS

The process of the invention uses a mixed oxide of a Group IVB metal and cerium as a solid acid catalyst for the cleavage of cumene hydroperoxide into phenol and acetone.

The present catalyst may have a calculated mole ratio, expressed in the form of $XO_2/CeO_n$ where X is at least one Group IVB metal (i.e., Ti, Zr, and Hf), of up to 1000, e.g., up to 300, e.g., from 2 to 100, e.g., from 4 to 80, although it is to be appreciated that these forms of oxides, i.e., $XO_2$ and $CeO_n$, may not actually be present in the catalyst of the invention.

The Group IVB metal oxide is preferably selected from titania, zirconia and hafnia, with zirconia being most preferred. The Group IVB and cerium metal species present in the final catalyst are not limited to any particular valence state and may be present in any positive oxidation value possible for the respective species.

Suitable sources of the Group IVB metal oxide include compounds capable of generating such oxides during calcination with ceria, such as oxychlorides, chlorides, and nitrates. Alkoxides may also be used as the sources of the Group IVB metal oxide, for example zirconium n-propoxide and titanium i-propoxide. A preferred source of the Group IVB metal oxide is hydrated zirconia. The expression, hydrated zirconia, is intended to connote a material comprising zirconium atoms covalently linked to other zirconium atoms via bridging oxygen atoms and further comprising available surface hydroxyl groups. These available surface hydroxyl groups are believed to react with the ceria species to form the present acidic catalyst component. Hydrated zirconia can be formed by precalcination of $Zr(OH)_4$ at a temperature of about 100° C. to about 400° C.

While not being bound by this chemistry, it is speculated that interactions between the zirconia and ceria may be similar to those between zirconia and tungstate oxides, and therefore hydrothermal treatment of the hydrated Group IVB metal oxide, such as hydrated zirconia, could promote the interaction with the ceria species. The hydrothermal treatment conditions may include a temperature of at least 80° C., e.g., at least 100° C. The hydrothermal treatment may take place in a sealed vessel at greater than atmospheric pressure. However, a preferred mode of treatment involves the use of an open vessel under reflux conditions. Agitation of hydrated Group IVB metal oxide in the liquid medium, e.g., by the action of refluxing liquid and/or stirring, promotes the effective interaction of the hydrated oxide with the liquid medium. The duration of the contact of the hydrated oxide with the liquid medium may be at least 1 hour, e.g., at least 8 hours. The liquid medium for this treatment may have a pH of about 7 or greater, e.g., 9 or greater. Suitable liquid media include water, hydroxide soglutions (including hydroxides of $NH_4^+$, $Na^+$, $K^+$, $Mg^{2+}$, and $Ca^{2+}$), carbonate and bicarbonate solutions (including carbonates and bicarbonates of $NH_4^+$, $Na^+$, $K^+$, $Mg^{2+}$, and $Ca^{2+}$), pyridine and its derivatives, and alkyl/hydroxyl amines.

Suitable sources of cerium oxide include, but are not limited to, oxygen-containing salts, for example cerium sulfate.

In one embodiment of the invention, the catalyst is prepared by impregnating a hydrothermally treated hydrated oxide of the Group IVB metal with an aqueous solution containing cerium ions, followed by drying. The resulting catalyst precursor is then calcined in the manner described below.

In another embodiment of the invention, the catalyst is prepared by co-precipitation from a liquid mixture of cerium and Group IVB ions followed by calcination of the resulting catalyst precursor in the manner described below. The liquid mixture can be prepared by combining a first liquid solution comprising a source of Group IVB metal oxide with a second liquid solution comprising a source of cerium ions. This combination of two solutions takes place under conditions sufficient to cause co-precipitation of the catalyst precursor as a solid from the liquid medium. alternatively, the source of the Group IVB metal oxide and the source of the cerium ions may be combined in a single solution. This solution may then be subjected to conditions sufficient to cause co-precipitation of the catalyst, such as by the addition of a precipitating reagent, such as ammonia, to the solution. Water is a preferred solvent for these solutions. The pH at which the liquid mixture is maintained during co-precipitation appears to be important in determining the activity of the final catalyst and hence the pH should be maintained below 9, preferably between 3 and 8, and most preferably between 6 and 8. The temperature at which the liquid medium is maintained during the co-precipitation is generally less than about 200° C. and is preferably from about 50° C. to about 100° C.

Calcination of the catalyst precursor is effected, preferably in an oxidizing atmosphere, at a temperature of at least 400° C., preferably at least 500° C., and more preferably from about 550° C. to about 800° C., and most preferably from about 600° C. to about 700° C. The calcination time may be up to 48 hours, preferably for about 0.5–24 hours, and more preferably for about 1.0–10 hours. In a most preferred embodiment, calcination is carried out at about 700° C. for about 1 to about 3 hours.

The resultant catalyst may be subjected to a final calcination under conventional conditions in order to dehydrate the catalyst and to confer the required mechanical strength on the catalyst. Prior to use the catalyst may be subjected to presulfiding, e.g., by heating in the presence of hydrogen sulfide, to convert oxide forms of the metal components to their corresponding sulfides.

Other metals, such as metals of Groups IB, VIIB and VIII, and preferably iron, manganese and/or copper, may optionally be added to the present catalyst to alter its catalytic properties.

The present catalyst may be composited with a matrix material to form the finished form of the catalyst and for this purpose conventional matrix materials such as alumina, silica-alumina and silica are suitable with preference given to silica as a non-acidic binder. Other binder materials may be used, for example, titania, zirconia and other metal oxides or clays. The active catalyst may be composited with the matrix in amounts from 80:20 to 20:80 by weight, e.g., from 80:20 to 50:50 active catalyst:matrix. Compositing may be done by conventional means including mulling the materials together followed by extrusion or pelletizing into the desired finished catalyst particles.

The cleavage reaction of the invention is effected by contacting the cumene hydroperoxide with the solid oxide catalyst described above in the liquid phase at a temperature of 20 to 150° C., preferably 40 to 120° C., a pressure of atmospheric to 1000 psig, preferably atmospheric to 400 psig. To effect the contacting of the cumene hydroperoxide, the solid oxide catalyst described above may be contained in a stationary or fluidized bed, and the contacting operation may take place continuously or batch-wise. If the contacting takes place continuously, the LHSV based on cumene hydroperoxide is within the range of 0.1 to 100 $hr^{-1}$, preferably 1 to 50 $hr^{-1}$. If the contacting takes place batch-wise, the residence time is within the range of 1 to 360 min, preferably 1 to 180 min. The cumene hydroperoxide is preferably dissolved in an organic solvent inert to the cleavage reaction, such as benzene, toluene, cumene and most preferably acetone. The use of a solvent is preferred so as assist in dissipating the heat of reaction (about 60 kcal/mol).

The invention will now be more particularly described with reference to the following Examples.

EXAMPLE 1

500 g of $ZrOCl_2.8H_2O$ and 32 g of cerium sulfate were dissolved with stirring in 3.0 liters of distilled water. Another solution containing 260 g of concentrated $NH_4OH$ and 2.94 liters of distilled water was prepared. Both solutions were combined with stirring. The pH of this combined mixture was adjusted to 8 with the addition of conc. $NH_4OH$. This slurry was then put in polypropylene bottles and placed in a steambox (100° C.) for 72 hours. The product formed was recovered by filtration, washed with excess water, and dried overnight at 85° C. A portion of this catalyst was calcined to 700° C. in flowing air for 3 hours to produce an acidic oxide catalyst containing a nominal 5% Ce on zirconia.

EXAMPLE 2

To a 250-ml round bottom flask fitted with a condenser, stirrer and dropping funnel, and located in a water bath for temperature control, was charged a mixture of 100.0 g of acetone and 1.00 g of the catalyst of Example 1. The mixture was heated to reflux (57° C.) with stirring, and 50.0 g of "80%" cumene hydroperoxide (CHP) solution (analyzed as 80.8% CHP, 7.7% cumene, 6.9% 2-phenyl-2-propanol, 2.1% acetophenone) was added dropwise at an approximate rate of 2 g/min. Following addition of the CHP solution, small samples (~0.2 ml) of the reactant solution were withdrawn at regular intervals, filtered, and analyzed by gas chromatography. The table below shows the composition (mass %) of the reactant solution at 1 and 3 hours after the addition of the CHP was complete.

|  | Feed | 1 hr | 3 hr |
|---|---|---|---|
| Acetone | 66.67 | 76.63 | 77.43 |
| Mesityl Oxide | 0.0 | 0.00 | 0.00 |
| Cumene | 2.56 | 2.61 | 2.63 |
| Phenol | 0.09 | 15.17 | 16.78 |
| α-Methyl Styrene | 0.07 | 0.20 | 0.37 |
| Acetophenone | 0.70 | 1.34 | 0.88 |
| 2-Phenyl-2-Propanol | 2.36 | 1.82 | 1.48 |
| Cumene Hydroperoxide | 26.93 | 1.54 | 0.06 |
| CHP Conversion |  | 94.3% | 99.8% |

EXAMPLE 3

Five hundred grams of $ZrOCl_2.8H_2O$ and 64 g of cerium sulfate were dissolved with stirring in 3.0 liters of distilled water. Another solution containing 260 g of conc. $NH_4OH$ and 3.0 liters of distilled water was prepared. Both solutions were heated to 60° C. These two heated solutions were combined at the rate of 50 ml/min using a nozzle mixer. The pH of this combined mixture was adjusted to 8 with the addition of conc. $NH_4OH$. This slurry was then put in polypropylene bottles and placed in a steambox (100° C.) for 72 hours. The product formed was recovered by filtration, washed with excess water, and dried overnight at 85° C. A portion of this catalyst was calcined to 700° C. in flowing air for 3 hours to produce an acidic oxide catalyst containing a nominal 10% Ce on zirconia.

EXAMPLE 4

To a 250-ml round bottom flask fitted with a condenser, stirrer and dropping funnel, and located in a water bath for temperature control, was charged a mixture of 100.0 g of acetone and 1.00 g of the catalyst of Example 3. The mixture was heated to reflux (57° C.) with stirring, and 50.0 g of "80%" cumene hydroperoxide (CHP) solution (analyzed as 80.8% CHP, 7.7% cumene, 6.9% 2-phenyl-2-propanol, 2.1% acetophenone) was added dropwise at an approximate rate of 2 g/min. Following addition of the CHP solution, small samples (~0.2 ml) of the reactant solution were withdrawn at regular intervals, filtered, and analyzed by GC.

The table below shows the composition (mass %) of the reactant solution at 1 and 3 hours after the addition of the CHP was complete.

|  | Feed | 1 hr | 3 hr |
|---|---|---|---|
| Acetone | 66.67 | 70.01 | 72.36 |
| Mesityl Oxide | 0.0 | 0.00 | 0.00 |
| Cumene | 2.56 | 2.59 | 2.60 |
| Phenol | 0.09 | 5.38 | 8.87 |
| α-Methyl Styrene | 0.07 | 0.17 | 0.20 |
| Acetophenone | 0.70 | 1.32 | 1.63 |
| 2-Phenyl-2-Propanol | 2.36 | 2.26 | 2.19 |
| Cumene Hydroperoxide | 26.93 | 17.49 | 11.26 |
| CHP Conversion |  | 35.1% | 58.2% |

EXAMPLE 5

50 g of $ZrOCl_2.8H_2O$ was dissolved with stirring in 300 ml of distilled water. Another solution containing 3.2 grams of cerium sulfate and 300 ml of distill water was prepared. Both solutions were combined with stirring. The pH of this combined mixture was adjusted to 3 with the addition of a concentrated $NH_4OH$ solution. This slurry was then put in polypropylene bottles and placed in a steambox (100° C.) for 72 hours. The product formed was recovered by filtration, washed with excess water, and dried overnight at 85° C. A portion of this catalyst was calcined to 700° C. in flowing air for 3 hours to produce an acidic oxide catalyst containing a nominal 5% Ce on zirconia.

EXAMPLE 6

To a 250-ml round bottom flask fitted with a condenser, stirrer and dropping funnel, and located in a water bath for temperature control, was charged a mixture of 100.0 g of acetone and 1.00 g of the catalyst of Example 5. The mixture was heated to reflux (57° C.) with stirring, and 50.0 g of "80%" cumene hydroperoxide (CHP) solution (analyzed as 80.8% CHP, 7.7% cumene, 6.9% 2-phenyl-2-propanol, 2.1% acetophenone) was added dropwise at an approximate rate of 2 g/min. Following addition of the CHP solution, small samples (~0.2 ml) of the reactant solution were withdrawn at regular intervals, filtered, and analyzed by gas chromatography. The table below shows the composition (mass %) of the reactant solution at 1.0 and 3.25 hours after the addition of the CHP was complete.

|  | Feed | 1 hr | 3 hr |
|---|---|---|---|
| Acetone | 66.67 | 76.02 | 77.30 |
| Mesityl Oxide | 0.0 | 0.00 | 0.00 |
| Cumene | 2.56 | 2.58 | 2.61 |
| Phenol | 0.09 | 15.31 | 16.73 |
| α-Methyl Styrene | 0.07 | 0.21 | 0.28 |
| Acetophenone | 0.70 | 1.50 | 0.96 |
| 2-Phenyl-2-Propanol | 2.36 | 1.81 | 1.51 |
| Cumene Hydroperoxide | 26.93 | 3.27 | 0.14 |
| CHP Conversion |  | 87.9% | 99.5% |

EXAMPLE 7

500 g of $ZrOCl_2.8H_2O$ and 32 g of cerium sulfate were dissolved with stirring in 3.0 liters of distilled water. Another solution containing 260 g of concentrated $NH_4OH$ and 2.94 liters of distilled water was prepared. Both solutions were combined with stirring. The pH of this combined mixture was adjusted to 8 with the addition of conc. $NH_4OH$. This slurry was then put in polypropylene bottles and placed in a steambox (100° C.) for 72 hours. The product formed was recovered by filtration, washed with excess water, and dried overnight at 85° C. A portion of this catalyst was calcined to 600° C. in flowing air for 3 hours to produce an acidic oxide catalyst containing a nominal 5% Ce on zirconia.

EXAMPLE 8

To a 250-ml round bottom flask fitted with a condenser, stirrer and dropping funnel, and located in a water bath for temperature control, was charged a mixture of 100.0 g of acetone and 1.00 g of the catalyst of Example 7. The mixture was heated to reflux (57° C.) with stirring, and 50.0 g of "80%" cumene hydroperoxide (CHP) solution (analyzed as 80.8% CHP, 7.7% cumene, 6.9% 2-phenyl-2-propanol, 2.1% acetophenone) was added dropwise at an approximate rate of 2 g/min. Following addition of the CHP solution, small samples (~0.2 ml) of the reactant solution were withdrawn at regular intervals, filtered, and analyzed by gas chromatography. The table below shows the composition (mass %) of the reactant solution at 1 and 3 hours after the addition of the CHP was complete.

|  | Feed | 1 hr | 3 hr |
|---|---|---|---|
| Acetone | 66.67 | 70.07 | 73.14 |
| Mesityl Oxide | 0.0 | 0.00 | 0.00 |
| Cumene | 2.56 | 2.52 | 2.54 |
| Phenol | 0.09 | 5.25 | 9.28 |
| α-Methyl Styrene | 0.07 | 0.18 | 0.21 |
| Acetophenone | 0.70 | 1.48 | 1.89 |
| 2-Phenyl-2-Propanol | 2.36 | 2.22 | 2.09 |
| Cumene Hydroperoxide | 26.93 | 17.51 | 9.72 |
| CHP Conversion |  | 34.98% | 63.7% |

What we claim is:

1. A process for producing phenol and acetone from cumene hydroperoxide comprising the step of contacting cumene hydroperoxide with a solid-acid catalyst comprising a mixed oxide of cerium and a Group IVB metal.

2. The process of claim 1, wherein said Group IVB metal is zirconium.

3. The process of claim 1, wherein said solid acid catalyst is produced by calcining a catalyst precursor comprising a source of a Group IVB metal oxide with a source of cerium oxide at a temperature of at least 400° C.

4. The process of claim 3, wherein said temperature is at least 500° C.

5. The process of claim 3, wherein said temperature is 600–700° C.

6. The process of claim 1, wherein said catalyst precursor is precipitated from a liquid mixture containing ions of cerium and said Group IVB metal at a pH less than 9.

7. The process of claim 6, wherein said pH is 3 to 8.

8. The process of claim 1, wherein said solid acid catalyst also contains a metal selected from Groups IB, VIIB, or VII of the Periodic Table.

9. The process of claim 1, wherein said contacting step is conducted at a temperature of 20 to 150° C. and a pressure of atmospheric to 1000 psig.

10. The process of claim 1, wherein said contacting step is conducted at a temperature of 40 to 120° C. and a pressure of atmospheric to 400 psig.

* * * * *